US008693700B2

(12) United States Patent
Bakalos et al.

(10) Patent No.: US 8,693,700 B2
(45) Date of Patent: Apr. 8, 2014

(54) ADAPTIVE FEED-FORWARD NOISE REDUCTION

(75) Inventors: Pericles Bakalos, Maynard, MA (US); Anand Parthasarathi, Ashland, MA (US)

(73) Assignee: Bose Corporation, Framingham, MA (US)

( * ) Notice: Subject to any disclaimer, the term of this patent is extended or adjusted under 35 U.S.C. 154(b) by 503 days.

(21) Appl. No.: 13/077,190

(22) Filed: Mar. 31, 2011

(65) Prior Publication Data

US 2012/0250873 A1 Oct. 4, 2012

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04R 29/00*** | (2006.01) |
| ***H04R 1/10*** | (2006.01) |

(52) U.S. Cl.

USPC ....... 381/71.6; 381/71.1; 381/71.2; 381/71.8; 381/71.11; 381/71.12; 381/58; 381/74

(58) Field of Classification Search

USPC ................. 381/71.6, 71.1, 71.2, 71.8, 71.11, 381/71.12, 58, 74

See application file for complete search history.

(56) References Cited

U.S. PATENT DOCUMENTS

| | | | | |
|---|---|---|---|---|
| 5,652,799 | A | 7/1997 | Ross et al. | |
| 5,852,667 | A | 12/1998 | Pan et al. | |
| 6,118,878 | A | 9/2000 | Jones | |
| 6,275,592 | B1 | 8/2001 | Vartiainen | |
| 6,449,369 | B1 * | 9/2002 | Carme et al. | 381/71.12 |
| 6,522,753 | B1 | 2/2003 | Matsuzawa et al. | |
| 7,103,188 | B1 | 9/2006 | Jones | |
| 2007/0098119 | A1 | 5/2007 | Stothers et al. | |
| 2010/0061564 | A1 * | 3/2010 | Clemow et al. | 381/71.6 |
| 2010/0322430 | A1 | 12/2010 | Isberg | |

FOREIGN PATENT DOCUMENTS

| | | |
|---|---|---|
| GB | 2455821 | 6/2009 |

* cited by examiner

*Primary Examiner* — Vivian Chin
*Assistant Examiner* — Douglas Suthers
(74) *Attorney, Agent, or Firm* — Occhiuti & Rohlicek LLP

(57) ABSTRACT

In an aspect, the invention features an active noise reduction device including an electronic signal processing circuit. The electronic signal processing circuit includes a first input for accepting a first signal, a second input for accepting a second signal, an output for providing a third signal, a feed-forward path from the first input to the output, and a feed-forward controller for determining the control parameter by calculating a control signal using the first signal and the second signal and then using the control signal to determine the control parameter. The feed-forward path includes a fixed compensation linear filter and a variable compensation filter having an input for receiving a control parameter that applies a selected linear filter from a family of linear filters that vary in both gain and spectral shape and are selectable by the control parameter.

17 Claims, 5 Drawing Sheets

FIG. 1 – Prior Art –

FIG. 2 – Prior Art –

ADAPTIVE FEED-FORWARD NOISE REDUCTION

FIELD OF DISCLOSURE

This invention relates to adaptive feed-forward noise reduction.

BACKGROUND

The presence of ambient acoustic noise in an environment can have a wide range of effects on human hearing. Some examples of ambient noise, such as engine noise in the cabin of a jet airliner can cause minor annoyance to a passenger. Other examples of ambient noise, such as a jackhammer on a construction site can cause permanent hearing loss.

Techniques for the reduction of ambient acoustic noise are an active area of research, providing benefits such as more pleasurable hearing experiences and avoidance of hearing losses.

In one of the simplest noise reduction techniques, an earcup can be designed such that its size, fit to a wearer's head, and sound absorption properties cause passive attenuation of ambient acoustic noise. For example, hearing protection ear muffs such as those worn on the flight deck of an aircraft carrier can be designed to absorb and reflect potentially damaging acoustic noise.

To further improve acoustic noise reduction, more sound absorbing material can be used, the size of the earcup can be increased, or the fit of the earcup to the wearer's head can be improved. However, there is a tradeoff between the bulkiness and comfort of hearing protection devices such as ear muffs and the amount of passive noise attenuation that they provide. To thoroughly reduce ambient noise, the ear muffs may need to be unreasonably large and/or uncomfortable. Instead, designers of such devices specify an acceptable amount of noise that is allowed to reach the wearer of the device.

Passive noise reduction is most effective at high frequencies (e.g., those frequencies that lie above 3 kHz) with reduced effectiveness below those frequencies. Furthermore, the effectiveness of passive noise reduction is susceptible to factors related to the coupling of the device onto the ear. Factors such as the shape of a user's head, the presence of glasses, etc. all affect the seal of the device around the ear, allowing additional noise to reach the wearer of the device.

Due to the shortcomings of passive noise reduction techniques, some designers of noise reduction systems use electronics to actively reduce noise. Referring to FIG. 1, an exemplary acoustic noise cancellation system 100 incorporates electronics that are designed to detect unwanted acoustic noise 104 that is not cancelled by passive attenuation provided by an earcup 101. The system 100 then uses a feed-back path to cancel the detected noise by creating an "anti-noise" signal (i.e., a signal that is equal and opposite to the detected noise). For example, a simple feed-back path 114 may be established by using a microphone 106 to sense unwanted acoustic noise in a cavity formed by a coupling of the earcup 101 and a wearer's head 109, and convert it to an electrical signal. The electrical signal is passed to a feed-back compensator 110 where it is amplified and phase inverted to generate the anti-noise signal. The anti-noise signal is then presented to the wearer's ear 108 using a transducer such as a headphone driver 112. Within the cavity, the transduced anti-noise signal and the unwanted acoustic noise 104 combine destructively, resulting in reduction of the net acoustic noise inside the earcup. This type of feed-back noise reduction is typically most effective at the low and middle audio frequency range (e.g., less than 1 kHz). It is difficult to increase this bandwidth due to limits placed on the acoustic system in terms of acoustic transport delay.

Feed-back active noise reduction systems such as the system presented in FIG. 1 typically exhibit a region of poor attenuation around 1 kHz (or in the "mid band"). As mentioned above, this is due to the passive attenuation being most effective at frequencies greater than 3 kHz and the feed-back attenuation being most effective at frequencies less than 1 kHz.

One solution for increasing noise attenuation around 1 kHz is a feed-forward filter spanning the aforementioned frequency band. Referring to FIG. 2, another exemplary acoustic noise cancellation system 200 includes an open loop feed-forward path 220 in addition to the previously presented feed-back path 114 to improve the attenuation of unwanted acoustic noise 104. The feed-forward path 220 senses the unwanted acoustic noise 104 in the environment outside of the earcup 101 using a second microphone 216 and converts it to an electrical signal. The feed-forward path 220 then processes the electrical signal using a fixed feed-forward compensator 218 which filters the electrical signal. The filter characteristic of the fixed feed-forward compensator 218 represents the typical passive attenuation provided by the earcup 101. The filtered electrical signal is used to create an anti-noise signal that is an estimate of the inverse of the noise that is not passively attenuated by the earcup 101. The anti-noise signal is presented to the wearer's ear 108 using a transducer such as the headphone driver 112. This method of feed-forward filtering can be more effective than the passive and feed-back attenuation in the 1 kHz region. at the frequency range that the passive and feed-back attenuation is ineffective (i.e., 1 kHz to 3 kHz).

Due to their open loop designs, the aforementioned systems are not capable of adapting to changes that occur in more dynamic environments. In particular, changes to the fit due to inconsistent coupling of the earcup 101 to the head of the earphone wearer 109 can degrade the noise attenuation performance of such systems.

Some adaptive noise cancellation systems actively compensate for dynamically changing aspects such as coupling. For example, a system may use an adaptive algorithm such as the LMS algorithm to continually adjust the coefficients of a feed-back and/or feed-forward filter based on a cost function derived from the amount of noise sensed near the wearer's ear. While such systems may be effective, they can require complex, power intensive hardware and significant processing time for measuring noise, then calculating and synthesizing appropriate anti-noise signals in real time. Furthermore, the speed of convergence of the LMS algorithm can be slow in the presence of non-stationary noise and at high frequencies. Thus, such a system may be impractical for small, low cost, low power applications such as consumer headphones and earphones.

There is a need for a simple, fast, and low power active noise reduction system that is capable of compensating for variations due to changes in coupling.

SUMMARY

In an aspect, the invention features an active noise reduction device including an electronic signal processing circuit. The electronic signal processing circuit includes a first input for accepting a first signal, a second input for accepting a second signal, an output for providing a third signal, a feed-forward path from the first input to the output, and a feed-forward controller for determining the control parameter by calculating a control signal using the first signal and the second signal and then using the control signal to determine the control parameter. The feed-forward path includes a fixed compensation linear filter and a variable compensation filter having an input for receiving a control parameter that applies a selected linear filter from a family of linear filters that vary in both gain and spectral shape and are selectable by the control parameter.

One or more of the following features may be included:

Embodiments may include a device body configured to form a cavity when coupled to the anatomy of a wearer, a first microphone configured to sense the sound pressure level outside of the cavity and generate the first signal, a second microphone configured to sense the sound pressure level inside of the cavity and generate the second signal, and a driver configured to receive the third signal and provide sound pressure to the inside of the cavity.

The device body may include an earcup. The device body may include an in-ear headphone interface. Each linear filter in the family of linear filters may represent a deviation from an average of a plurality of different positions of the device body on the anatomy of the wearer. Monotonically changing the value of the control parameter may cause the gain at any particular frequency of the frequency response of the selected linear filter to change monotonically. Embodiments may include a feed-back path from the second input to the output, the feed-back path including a feed-back compensation filter.

The outputs of the variable compensation filter and the feed-back compensation filter may be combined to generate the third signal. The feed-forward controller may include an error minimization algorithm that determines the control parameter. The error minimization algorithm may be the LMS algorithm. Embodiments may include a band limiter configured to band limit the first signal and the second signal before they are provided to the feed-forward controller. The parameter may include a plurality of values.

In another aspect, the invention features a method for active noise reduction including accepting a first signal from a first input, accepting a second signal from a second input, producing a third signal, and providing the third signal to an output. Producing the third signal includes processing the first signal using a feed-forward path from the first input to the output, the processing of the feed-forward path. The processing of the feed-forward path includes filtering using a fixed compensation filter, and filtering using a variable compensation filter controlled by a control parameter that applies a selected linear filter from a family of filters that vary in both gain and spectral shape and are selectable by the control parameter; and determining the control parameter that controls a feed-forward controller by calculating a control signal using the first signal and the second signal and then using the control signal to determine the control parameter.

One or more of the following features may be included:

Producing the third signal may include processing the second input using a feed-back path from the second input to the output. The second input may be processed in the feed-back path by a feed-back compensation filter. The output of the variable compensation filter and the feed-back compensation filter may be combined to form the third signal. The control signal may be determined using an error minimization algorithm. The error minimization algorithm may be the LMS algorithm. The first signal and the second signal may be band limited before they are provided to the feed-forward controller.

Other features and advantages of the invention are apparent from the following description, and from the claims.

DESCRIPTION

1 Overview

Figure 3:
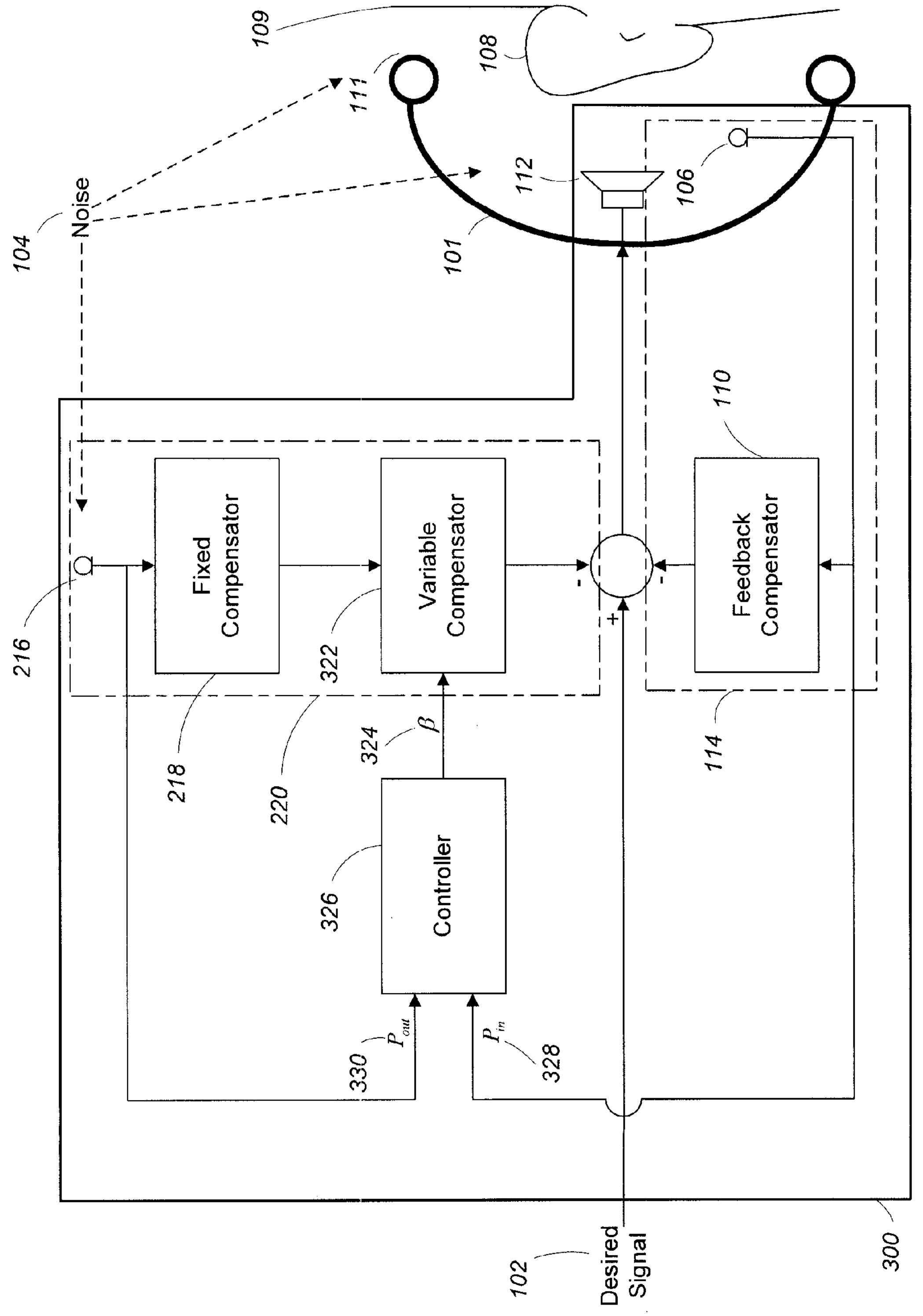
FIG. 3 is an active noise reduction system including a feed-back path and an adaptive feed-forward path.

Referring to FIG. 3, an embodiment of an active noise reduction system 300 is configured to cancel unwanted ambient noise, specifically in headphones. In the figure, a user 109 wears circumaural headphones over their ears 108 in an environment including ambient noise 104. A cavity is formed by coupling an earpiece 101 of the headphones to a user's head 109. Some portion of the ambient noise 104 transmits into the cavity through the material of the headphone earpiece 101 and some other portion of the ambient noise 104 transmits into the cavity through openings 111 caused by poor coupling between the user and the earpiece 101 called "leaks". (Note that word "leaks" should be understood only within the context of this description and not to connote properties where it is used in other contexts.)

The headphones include an electronic system 300 that is configured to sense the undesirable ambient noise 104 that is present both outside the earpiece 101 and inside the cavity that is formed by the earpiece 101 and generate an anti-noise signal to eliminate or mitigate an effect of the ambient noise 104 from the sound transmitted to the user's ear 108.

The system 300 includes a feed-forward path 220 and a feed-back path 114. Both paths generate anti-noise signals that reduce unwanted acoustic noise present within the earpiece 101 by destructive interference.

2 Feed Forward Path

In some examples, the feed-forward path senses the ambient noise 104 in the environment outside of the earpiece 101. For example, a transducer such as a second microphone 216 can be placed on the outer surface of the earpiece 101. The transducer 112 converts the sound pressure outside of the cavity into an electrical signal. The electrical signal representing the sound pressure level outside the cavity is passed to a fixed compensator 218.

2.1 Fixed Compensator

In some examples, the fixed compensator 218 is a filter with a fixed transfer function that is determined by the designer of the headphones. For example, the headphone designer may measure a series of on-head transfer functions, for example resulting from passive attenuation of the headphones over a large and varied population of users. Each user possesses unique characteristics that affect the coupling (or "fit) of the headphones over the user's ears. The coupling quality is affected by leaks caused by factors such as the presence of glasses, ear size, shape and size of the user's head, etc. The result of measuring the series of on-head transfer functions over the large population is called the "average leak". The average leak is used to determine the transfer function for the fixed compensator 218.

The transfer function of the fixed compensator 218 is determined such that the noise sensed by the second microphone 216 and filtered using the fixed compensator 218 is equal to the noise experienced by a user who embodies the average fit.

However, it is very unlikely that any one user exactly embodies the average fit. It is more likely that the coupling of the headphone earcups 101 and the user's ear 108 differs slightly from the average coupling. Therefore, the actual transfer function of the headphone earpieces 101 is somewhat different than those used to design the fixed compensator 218.

In some examples, difference in coupling between the actual fit and the average fit can be characterized by a point on a progression of compensator gain and/or compensator linear phase (i.e., delay).

2.2 Variable Compensator

To compensate for the difference in coupling between the actual fit and the average fit, a variable compensator 322 can be placed in cascade with the fixed compensator 218. In some examples, the variable compensator 322 compensates for variations in feed-forward attenuation due to leaks caused by changes in coupling by altering the transfer function of the feed-forward path 220. In some examples, a frequency independent gain change of the compensator 322 may provide sufficient alteration to mitigate the noise. More generally, in other examples, a parameter change to the compensator 322 linear transfer function is used.

In some examples, the filtered output of the fixed compensator 218 is passed to a variable compensator 322. The variable compensator 322 receives a single parameter β 324 from a controller 326 and uses the parameter to select a linear transfer function from a predefined family of transfer functions. The selected transfer function is applied in conjunction with the average fixed transfer function of the fixed compensator 218 to yield the overall feed-forward transfer function.

Figure 4:
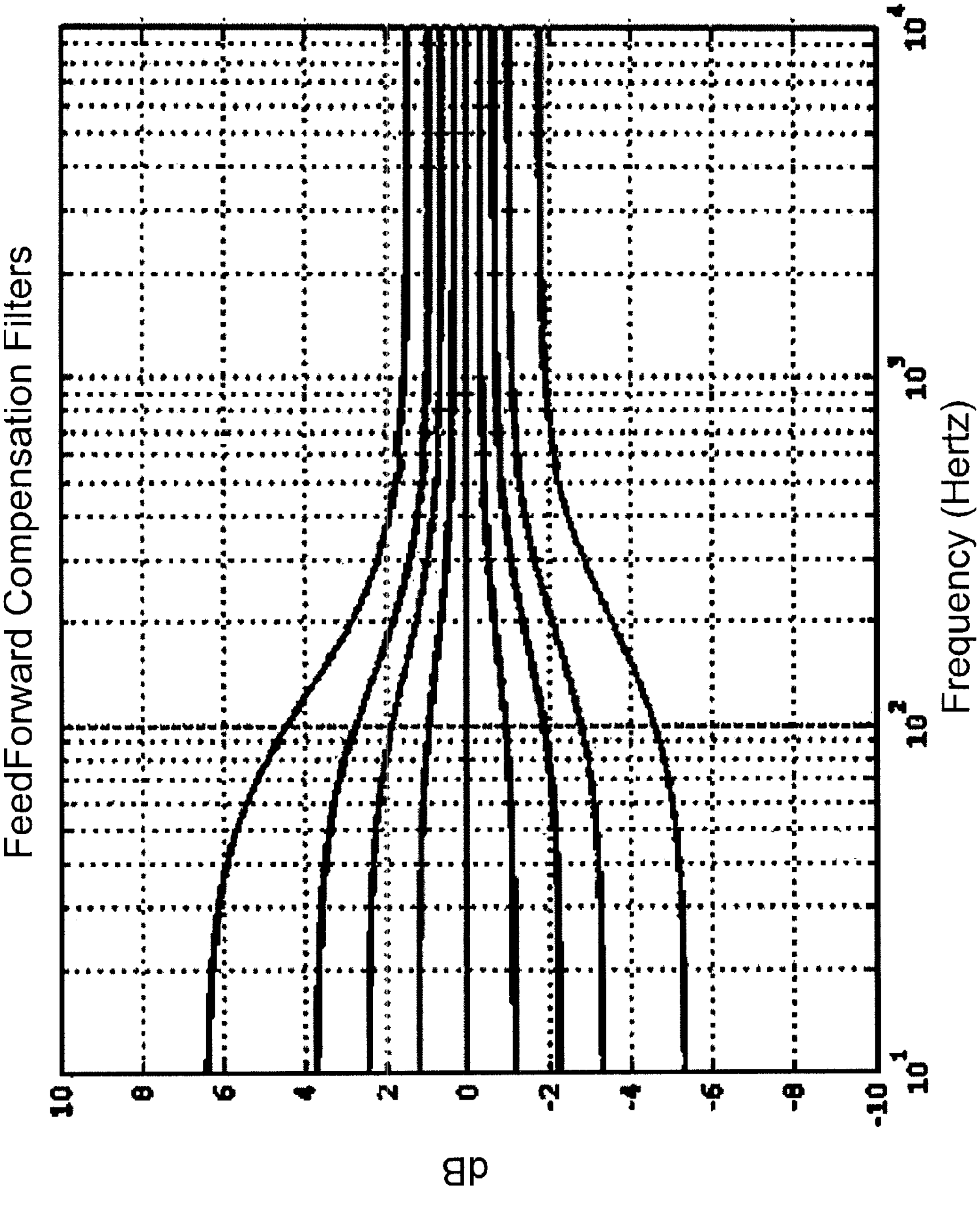
FIG. 4 is a graph showing a family of linear filters.

Referring to FIG. 4, one example of the magnitude frequency response of a family of linear filters that are included in the configuration of the variable compensator 322 is shown. Generally, each linear filter corresponds to a different degree of deviation of the actual user fit from the average. The characteristics of the family of linear filters depend on the fit and the fixed feed-back compensator 218 filter characteristic. In some examples, any change in one of these factors may change the characteristics of the family of linear filters.

Generally, families of linear filters of different examples share some common properties. In particular, the changes in low frequency gain are commonly greater than the changes in high frequency gain, each family of linear filters is broad band, and the frequency responses of the family of linear filters have monotonically increasing gain characteristics. In some examples, selection of which linear filter to use in the variable compensator 322 changes monotonically as the parameter β 324 changes monotonically. For example, the lowest value of β 324 selects the linear filter with the lowest frequency response gain. As β 324 increases, the linear filter with the second lowest frequency response gain is selected, and so on.

As is described further below, in some examples, once an optimal value of β 324 is reached, the overall slope of the phase characteristic of the variable compensator 322 is adjusted (i.e, the compensator 322 delay is adjusted) to further mitigate unwanted noise.

Again referring to FIG. 3, as described below, the controller 326 determines the parameter β 324 such that the selected linear transfer function best compensates for the difference between the actual transfer function of the coupled earpiece 101 and the transfer function of the fixed compensator 216.

Generally, the output of the variable compensator 322 is a better estimate of the noise 104 inside of the earpiece that is not passively attenuated than the output of the fixed compensator 218 alone.

2.3 Controller

The controller 326 receives inputs based on signals from the first microphone 106 and the second microphone 216. The signals from the microphones 106, 216 are used to determine the time-averaged pressure inside of the cavity of the earpiece $P_{in}$ 328 and the time-averaged pressure in the outside environment $P_{out}$ 330. The time-averaged values $P_{in}$ and $P_{out}$ are then provided to the controller 326. In some examples, $P_{in}$ 328 and $P_{out}$ 330 are obtained by measuring RMS pressure values within a narrow frequency band and then averaging the values over time. In other examples, the pressure measurements can be a combination of pressure values from multiple frequency bands, or broad-band.

In some examples, the controller 326 uses the ratio $$R = \left|\frac{P_{in} - P_{out}}{P_{out}}\right|$$

to represent average the difference between the pressure inside the cavity of the earpiece, $P_m$ 328 and the pressure in the outside environment $P_{out}$ 330.

For example, assuming that an $P_{out}$ 330=1 Pa and $P_{in}$ 328=0 (i.e., perfect attenuation), the ratio is R=|(0−1)/1|=1. Hence for average fit the ratio is 1. However, if the headphone fit is 'leakier' than the average fit, the attenuation inside will be less than perfect. For example, if $P_{in}$ 328=0.5 Pa. The ratio is R=|(0.5−1)/1|=0.5. Thus, for leakier fits, the ratio will range between 0 and 1.

If the headphone fit is 'tighter' than the average fit, the attenuation inside will also be less than perfect. However, since the feed forward path 220 is producing an anti noise signal, $P_{in}$ 328 will be out of phase compared to $P_{out}$ 330. For example, if $P_{in}$ 328=0.5 Pa, the ratio is R=[(−0.5−1)/1]=1.5. Thus, for tighter fits the ratio is >1, typically between 1 and 2.

The parameter β 324 is determined such that the calculated ratio approaches unity, thereby minimizing the pressure in the earcup cavity, $P_{in}$ 328.

The minimization process can be accomplished by an error minimization algorithm that automatically adjusts β 324 such that the optimum linear filter is selected from the family of linear filters included in the variable compensator 322.

For example, the minimization process may follow the following steps:

a. Calculate the ratio at iteration n, $R_n$.
b. If the value of $R_n$ is less than unity, then increase β by a predetermined increment. (e.g., β=β+0.5 dB).
c. If the value of $R_n$ is greater than unity, then decrease β by a predetermined increment. (e.g., β=β−0.5 dB).
d. After modifying β, allow a predetermined amount of time to elapse. (e.g., 100 ms).
e. The process of modifying the parameter β is then continually repeated, causing the selection of the variable compensator's 322 linear filter to continually change such that the ratio approaches unity.

The aforementioned ratio calculation and adaptation process is most effective when using only the feed-forward path 220 (i.e., no feed-back path 114 is present). This is due to the ratio assuming that only the feed-forward path 220 influences $P_{in}$ 328. Thus, if inside attenuation is also influenced by the feed-back path 114, the ratio can become less than unity, causing the minimization to erroneously continue to adjust the parameter, β 324. One advantage of the ratio calculation used in this example is that the direction of the desired parameter, β 324, change is automatically determined. This results in one less step in the minimization process.

In another example, the controller 326 calculates the ratio as:

$$\left|\frac{P_{in}}{P_{out}}\right|$$

An error minimization algorithm can then be used to automatically adjust the parameter β 324 such that an optimal linear filter is selected from the family of linear filters included in the variable compensator 322.

For example, the error minimization process may follow the following list of steps:

a. Calculate and store the ratio at iteration n, $R_n$.

b. Decrease β by a predetermined step size. (e.g., β=β−0.5 dB).

c. Allow a predetermined amount of time to elapse. (e.g., 100 ms).

d. Calculate and store the ratio at iteration n+1, $R_{n+1}$.

e. Compare $R_n$ to $R_{n+1}$ i. If $R_n$ is greater than $R_{n+1}$, decrease the parameter β. (e.g., β=β−0.5 dB).

ii. If $R_n$ is less than $R_{n+1}$, increase the parameter β. (e.g., β=β+0.5 dB).

In some examples, this process for selecting a parameter β 324 such that an appropriate linear filter is selected from the family of linear filters included in the variable compensator 322 occurs only once.

In other examples, a pre-determined error band, B, can be defined such that the parameter β will change if $|R_n-R_{n+1}|$ is greater than B.

This example of a pressure ratio calculation and adaptation process is effective for systems including only a feed-forward path 220, and systems including a combined feed-forward path 220 and feed-back path 114. However, this method does not determine the direction of the desired change in β 324 automatically. Instead, an extra step is added to the adaptation process to determine the parameter change direction.

One advantage of using $|P_{in}/P_{out}|$ is that the sensitivities of the microphones 106, 216 do not need to be matched or adjusted for the controller. Another advantage is that the algorithm is insensitive to common mode variations in $P_{in}$ and $P_{out}$. The idea is to decrease this ratio by automatically adjusting the linear filter selected from the family of linear filters included in the variable compensator 322 such that the ratio is minimized. Another advantage of using this ratio is that it also corrects for changes in the feed-back gain, since it is always attempting to minimize the pressure ratio $|P_{in}/P_{out}|$ In another example, instead of calculating a ratio between $P_{in}$ and $P_{out}$, the system uses $P_{in}$ as an error signal. As is the case with most feed-back/feed-forward noise reduction systems, if the system has adequate correlation between the noise reduction at the first microphone 106 and the ear 108, minimizing the error signal at the first microphone 106 will increase the noise reduction performance of the headphone.

A simple error minimization scheme is used to minimize the error signal by increasing or decreasing β and shifting the phase of the cancellation signal within a prescribed narrow band. A step size is initially chosen such that within a predetermined number of steps, the gain and phase adjustments will converge such that the error signal is minimized. For example the minimization algorithm may follow the following steps:

a. Read and store the current error signal RMS level.

b. Increment (or decrement) the parameter. (e.g., β=β+/−0.5 dB).

i. Read and store the new error signal (i.e., $P_{in}/P_{out}$ ratio) RMS level. Subtract the new error signal from the error signal read in step a.

c. If the error signal has increased, change the direction of parameter adjustment, increase the step size by a small amount (i.e., 0.5*β+β) for the first step in the opposite direction to get beyond the previous state, then lower the step size back to β and repeat. If the error signal has decreased, continue the parameter adjustment in the same direction.

d. Increment a counter to track the number of parameter changes. If the counter has reached a predetermined count, exit the parameter adjustment loop and enter the phase adjustment loop. The gain has now been adjusted such that the error signal is minimized to within +1−1 step size in gain.

e. Repeat steps a-e, except that the narrow band phase is now adjusted such that the error signal is minimized.

It should be noted that in the aforementioned algorithms, the controller 326 optionally adjusts β 324 only when the desired signal 102 is below a certain threshold. When the desired signal 102 is above the threshold (e.g., the wearer is listening to music), β 324 remains fixed. Fixing β 324 when the desired signal 102 is above the threshold prevents the controller 326 from adjusting β 324 in an attempt to cancel the desired signal 102 using the feed-forward path 220. In some examples, a switch activated optimization routine which mutes any audio input signals before optimizing the compensator can be used. After the optimization routine is completed, the audio signals are un-muted and the routine waits for the next switch activation.

2.4 Example Adaptive Gain Feed-Forward Path

In some examples, the controller 326 is configured based on the a-priori assumption that changes in the fit can be characterized as a change in the gain of the feed-forward path 220 filtering.

Figure 5:
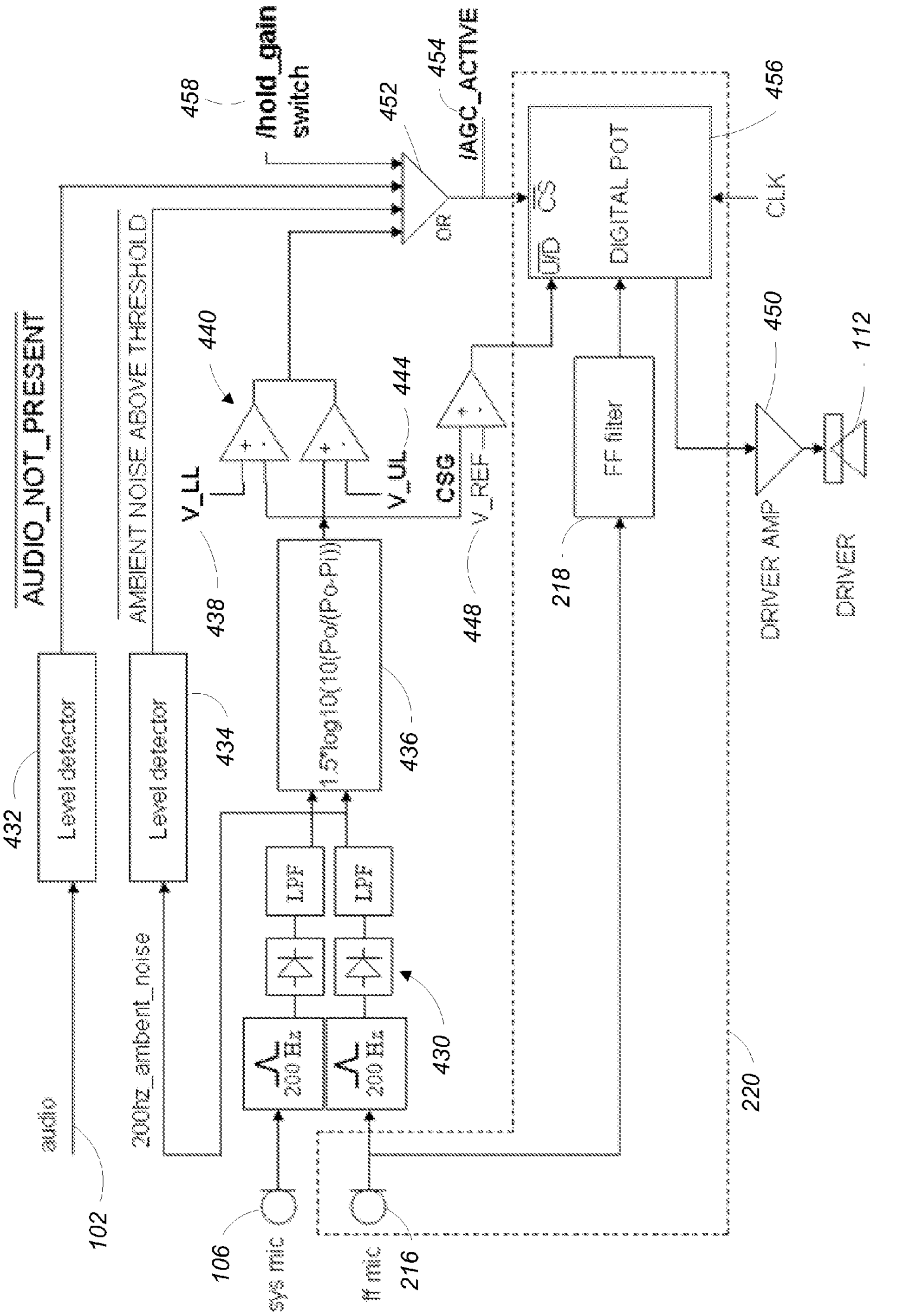
FIG. 5 is a detailed diagram of an adaptive feed-forward path.

Referring to FIG. 5, which shows a more detailed example of the system of FIG. 3, a feed-forward path 220 is configured to adaptively control the feed-forward cancellation signal magnitude by automatically adjusting a digital potentiometer 456 used as an attenuator to control the level of the feed-forward filter 218 output applied to the driver 112 such that a control signal generator 436 output moves into a range between preset upper and lower error bounds (V_LL 438, V_UL 444) of a window comparator 440. When the control signal generator 436 output is within the error bounds 438, 444, the gain of the attenuator 456 is held at the current value by outputting a voltage matching logic TRUE from the comparator 440, de-activating the negative-logic control signal (/CS) of the digital potentiometer attenuator 456. When the control signal 436 output is outside the error bounds 438, 444, the output of the comparator 440 matches logic FALSE, allowing the attenuator 456 to increase or decrease the gain. Additionally, the output of the control signal generator 436 is compared to a reference voltage 448 to determine the direction of gain control required and the direction is fed to the U/D (i.e., up or down direction) input of the attenuator 456.

In this example, a first level detector 432 receives a desired audio signal from an external device. The level detector 432 determines if the audio signal is above a predetermined level. A negative output “audio_not_present” is used so that the first level detector 432 output is FALSE when there is a signal, and TRUE if there is not a signal. This is then inverted to provide a negative logic control to the attenuator 456, so that gain is not adjusted if the audio signal is present, for reasons explained below.

A first microphone 106 senses the pressure $P_{in}$ inside of the headphone cavity (not shown). A second microphone 216 senses the pressure $P_{out}$ outside of the headphone cavity. Both sensed pressure signals are processed by a bank of filters and a rectifier/averager 430 which may include, for example, a band-pass filter and a low-pass filter.

The filtered pressure signal from the second microphone 216 is passed to a second level detector 434 which determines if the ambient noise is above a predetermined level. If so, the second level detector 434 output is TRUE, otherwise it is FALSE. As with the first level detector, this output is inverted to provide a negative logic control to the attenuator 456, preventing adjustment of the gain when the ambient noise is below the predetermined level.

The filtered pressure signals are then passed to the control signal generator 436 where a control signal is generated using, for example, the equation:

$$1.5 * \log_{10}\left(10\left(\frac{P_{out}}{P_{out} - P_{in}}\right)\right)$$

The result of the control signal generator 436 is passed to the window comparator 440 which determines if the result is within the upper and lower error bounds 438, 444. If the result is within the error bounds 438, 444, the output of the window comparator 440 is TRUE, preventing gain adjustment, otherwise it is FALSE.

The result of the control signal generator 436 is also compared to a reference voltage 448 that determines the direction of adjustment that needs to be made to the digital potentiometer attenuator 456.

The second microphone 216 signal is also passed to the fixed compensator 218 which filters the signal based on a fixed transfer function determined as described above. The result is passed to the signal input of the digital potentiometer attenuator 456.

The output of the first level detector 432, the second level detector 434, the window comparator 440, and a hold gain switch 458 (inverted) are all passed to a four input logical OR gate 452 where a logical OR is performed. The output of the OR is passed to the negative logic control input (/CS) of the digital potentiometer 456. If the output of the logical OR gate 452 is TRUE, automatic gain control is deactivated and the gain of the digital potentiometer 456 is not allowed to change. If all of the criteria are met (audio is not present, ambient is above threshold, control is out of range, and hold switch is open), then the OR result is FALSE, and the digital potentiometer 456 is allowed to change its gain. Other logic schemes may also be used.

The gain adjusted output of the attenuator 456 (i.e., the output of the feed-forward filter 218 after being attenuated) is passed to a driver amplifier 450 which amplifies the output such that it can be presented to the user (not shown) by a transducer such as a headphone driver 112. The audio signal 102 and feedback signal are also applied to the driver 112 through the amplifier 450, but are not shown in FIG. 5.

3 Feed-Back Path

In some examples, as was shown in FIG. 3, the feed-forward path 220 can be used in conjunction with a feed-back active noise reduction path 114 for the purpose of achieving greater total noise attenuation. When both the feed-forward path 220 and the feed-back path 114 are present, the feed-forward path 220 corrects for variations in the combined system by attempting to reduce the pressure sensed by the inside microphone 106.

Figure 1:
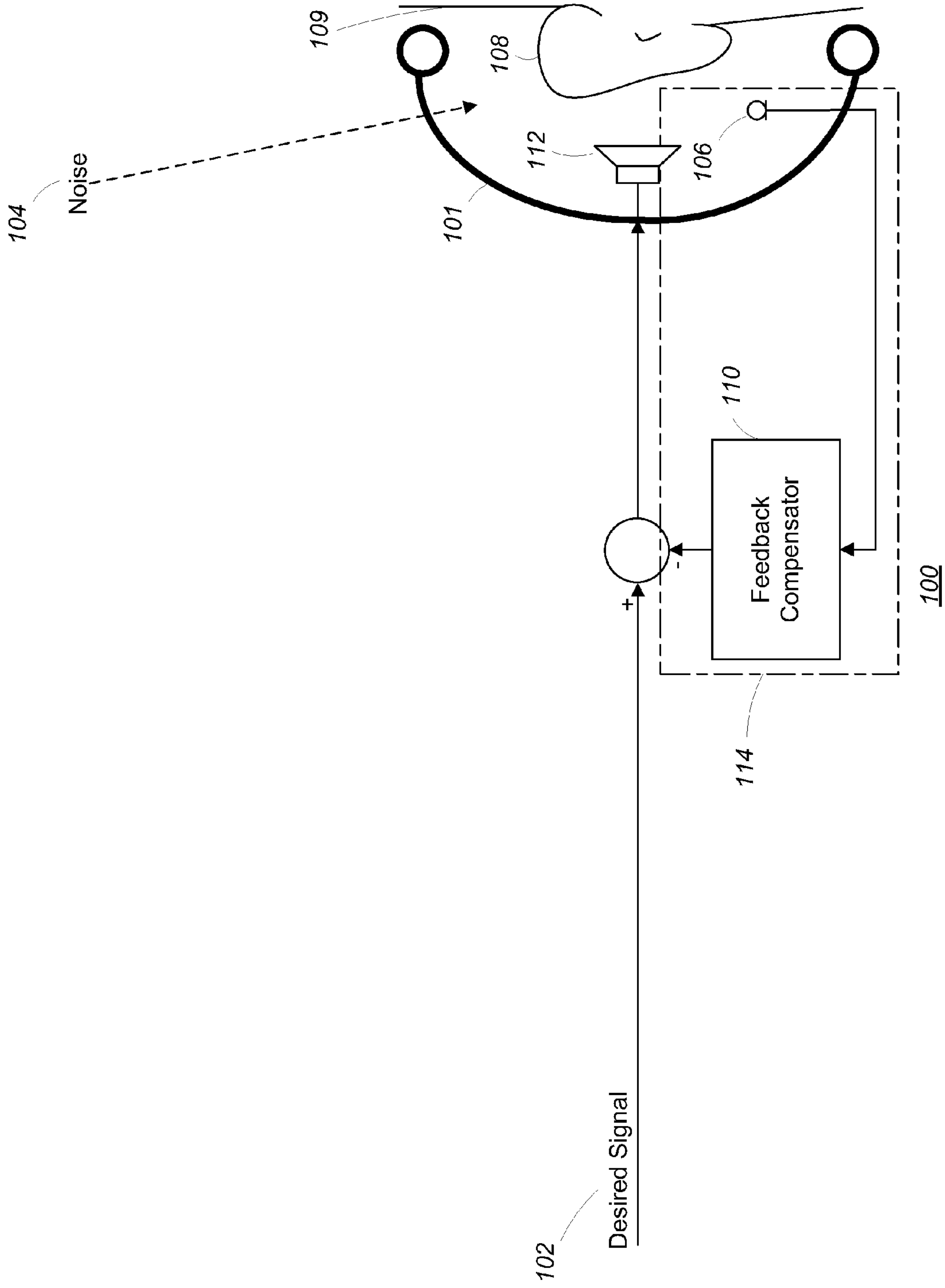
FIG. 1 is an active noise reduction system including a feed-back path.
Figure 2:
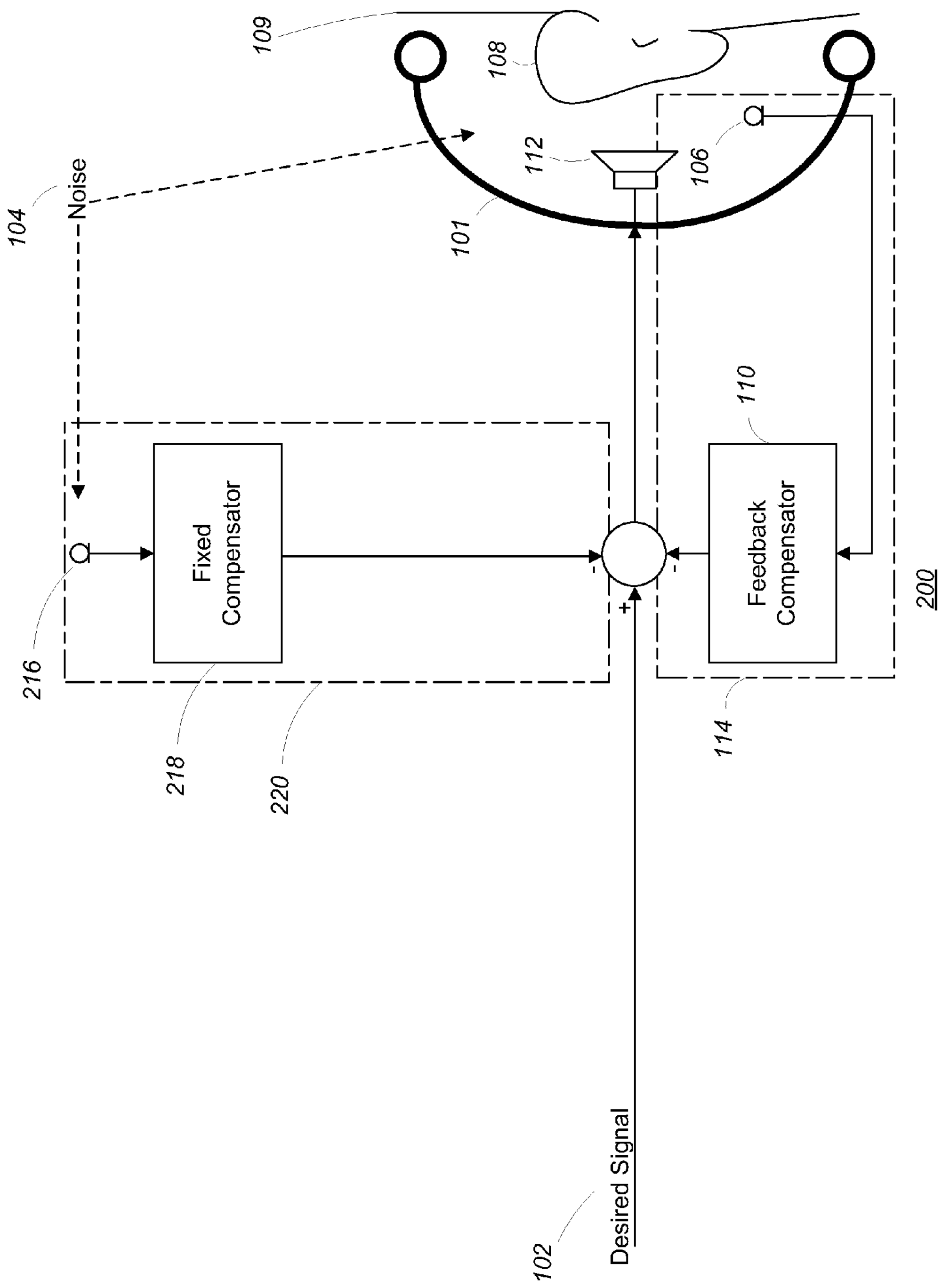
FIG. 2 is an active noise reduction system including a feed-back path and a feed-forward path.

As explained above with reference to FIG. 1, the feed-back path senses the noise transmitted into the cavity using a transducer such as a first microphone 106 located in the cavity. The microphone 106 converts the sound pressure level inside the cavity into an electrical signal. The electrical signal is passed along the feed-back path 114 to a feed-back compensator 110. The feed-back compensator 110 generates an anti-noise signal by, for example, amplifying the electrical signal and inverting its phase.

The output of the feed-back path 114 is combined with the output of the feed-forward path 220 and, in some cases, the input source 102. The combined signal is provided to a driver 112 in the earpiece 101 which transduces the signal into the pressure waves that the human ear 108 interprets as sound.

Since the sound produced by the driver 112 includes the anti-noise signal generated by the feed-forward and feed-back paths 114, 220 it closely resembles the inverse of the noise inside of the earpiece 101 within a limited bandwidth, and the user perceives a reduction in noise.

Using the feed-back active noise reduction path 114 in conjunction with the feed-forward path 220 is most effective when β 324 is adjusted according to the previously described $P_{in}/P_{out}$ ratio.

4 Acoustic Design

In some examples, headphones are specifically designed to create a low variation leakage characteristic by limiting the acoustic effects of fit variation. This establishment of the low variation leakage characteristic allows the same family of linear filters (i.e., those shown in FIG. 4) to be highly effective on a broad range of fits.

In some examples, the reduction in fit variation creates a stable relationship between the fit and the family of linear filters. In such examples, the single parameter β 324 can be used to choose the appropriate linear filter from the family of linear filters that compensates for the change in fit. This allows for adaptive noise reduction using a single parameter change.

5 Effect of External Audio

With a disturbance at $P_{in}$ due to external audio signal 102 being injected into the driver and detected by the feedback microphone 106, thus entering the feedback loop, the $P_{in}$ signal can exceed $P_{out}$ and cause the adaptive feed-forward controller to adapt in order to try and minimize the $P_{in}/P_{out}$ ratio. However, this will not cause matching of magnitude of the external noise originated cancellation signal to the inside pressure signal $P_{m}$, as the pressure inside the earcup is not entirely due to the external noise. However, if the audio signal is uncorrelated to the dynamics of the adaptive system, then there will be little or no adverse effects on system optimization for the $P_{in}/P_{out}$ error minimizer. One solution for this potential problem is to detect the presence of the audio signal and halt the gain adaptation while the audio signal is present, as shown in FIG. 5, or reset the feed-forward gain to the design average value for the expected range of fits in the presence of audio signal.

As was previously mentioned, in some examples, a user controlled switch can be used to simultaneously mute the external audio and active an adaptation process. The audio can then be automatically unmated when the adaptation process is complete.

6 Alternatives

An adaptive feed-forward path can be used in the same way to reduce unwanted acoustic noise in an in-ear headphone, an on-ear (supra-aural) headphone, or an around-ear (circum-aural) headphone.

In some examples, there could be a plurality of feed-forward microphones summed together to provide a spatial average of the ambient noise around the earcup. This signal is then input to the controller for adaptation of the feed-forward filter path.

In some examples, the headphones incorporate a mechanism to introduce audio or voice such that the headphones can be used for two-way communication.

In some examples, the electronic portion of the active noise reduction system is implemented on a stand-alone chip such as an application specific integrated circuit (ASIC). In other examples, a small, low pin count, low power microcontroller carries out the algorithm.

In some examples, an adaptive algorithm configured to minimize a cost function (e.g., the LMS algorithm) could be used as the minimization algorithm.

In some examples, the system is implemented using only analog electronics. In other examples, hybrid analog-digital (using analog filter and digital control signal generator) or a digital only (DSP) system may be used.

In some examples, the gain and phase of the forward-path filtering 220 can both be modified to correct for differences in fit. For example, a control parameter used to generate the gain change can also be used to generate the required phase adjustment. In a narrow band implementation the phase information, along with the gain change, can be used to achieve optimum noise cancellation.

In some examples, changes in β 324 can cause the filter characteristic of the variable compensator 322 to switch between pre-arranged, ordered discrete filter characteristics in a family of filter characteristics. In some examples, the family of filter characteristics can include many discrete filter characteristics that change very little from one filter characteristic to the next. In other examples, the family of filter characteristics can include fewer, and more spaced out discrete filter characteristics.

In some examples, the filter characteristics of the variable compensator 322 varies continuously as β 324 varies.

In some examples, the feed-forward path 220 can be determined from three transfer functions and is given by:

$$K_{ff} = \left[\frac{-G_{ne}}{G_{no}G_{de}}\right]$$

where, $G_{ne}$ is the external noise 104 to ear microphone 106 transfer function, $G_{no}$ is the external noise 104 to outside microphone 216 transfer function, and $G_{de}$ is the driver 112 to ear microphone 106 transfer function. The ratio $$\left[\frac{G_{ne}}{G_{no}}\right]$$

is an approximate measure of passive attenuation. Both $G_{de}$ and the ratio $$\left[\frac{G_{ne}}{G_{no}}\right]$$

change as a function of the headset 'fit' or 'leak' and hence the desired feed forward compensator changes as a function of 'fit' or 'leak'.

It is to be understood that the foregoing description is intended to illustrate and not to limit the scope of the invention, which is defined by the scope of the appended claims. Other embodiments are within the scope of the following claims.

What is claimed is:

1. An active noise reduction device comprising:
an electronic signal processing circuit including:
a first input for accepting a first signal;
a second input for accepting a second signal;
an output for providing a third signal; and
a feed-forward path from the first input to the output including:
a fixed compensation linear filter; and
a variable compensation filter having an input for receiving a control parameter that applies a selected linear filter from a family of linear filters that vary in both gain and spectral shape and are selectable by the control parameter; and
a feed-forward controller for determining the control parameter by calculating a control signal using the first signal and the second signal and then using the control signal to determine the control parameter
a device body configured to form a cavity when coupled to the anatomy of a wearer;
a first microphone configured to sense the sound pressure level outside of the cavity and generate the first signal;
a second microphone configured to sense the sound pressure level inside of the cavity and generate the second signal; and
a driver configured to receive the third signal and provide sound pressure to the inside of the cavity,
wherein each linear filter in the family of linear filters represents a deviation from an average of a plurality of different positions of the device body on the anatomy of the wearer.

2. The device of claim 1, wherein the device body comprises an earcup.

3. The device of claim 1, wherein the device body comprises an in-ear headphone interface.

4. The device of claim 1, wherein monotonically changing a value of the control parameter causes the gain at any particular frequency of the frequency response of the selected linear filter to change monotonically.

5. The device of claim 1, further comprising a feed-back path from the second input to the output, the feed-back path including a feed-back compensation filter.

6. The device of claim 5, wherein an output of the variable compensation filter and an output of the feed-back compensation filter are combined to generate the third signal.

7. The device of claim 1, wherein the feed-forward controller includes an error minimization algorithm that determines the control parameter.

8. The device of claim 7, wherein the error minimization algorithm is a least mean squares algorithm.

9. The device of claim 1, further comprising a band limiter configured to band limit the first signal and the second signal before they are provided to the feed-forward controller.

10. The active noise reduction device of claim 1, wherein the parameter includes a plurality of values.

11. A method for active noise reduction comprising:

accepting a first signal from a first input;

accepting a second signal from a second input;

producing a third signal; and providing the third signal to an output;

wherein producing the third signal comprises:

processing the first signal using a feed-forward path from the first input to the output, the processing of the feed-forward path including:

filtering using a fixed compensation filter; and filtering using a variable compensation filter controlled by a control parameter that applies a selected linear filter from a family of filters that vary in both gain and spectral shape and are selectable by the control parameter; and determining the control parameter by use of a feed-forward controller by calculating a control signal using the first signal and the second signal and then using the control signal to determine the control parameter wherein each linear filter in the family of linear filters represents a deviation from an average of a plurality of different positions of a device body on an anatomy of the wearer.

12. The method of claim 11, wherein producing the third signal further comprises processing the second input using a feed-back path from the second input to the output.

13. The method of claim 12, wherein the second input is processed in the feed-back path by a feed-back compensation filter.

14. The method of claim 13, wherein an output of the variable compensation filter and an output of the feed-back compensation filter are combined to form the third signal.

15. The method of claim 11, further comprising determining the control parameter using an error minimization algorithm.

16. The method of claim 15, wherein the error minimization algorithm is a least mean squares algorithm.

17. The method of claim 11, further including band limiting the first signal and the second signal before providing them to the feed-forward controller.

* * * * *